United States Patent [19]

Kudamatsu et al.

[11] Patent Number: 4,497,804
[45] Date of Patent: Feb. 5, 1985

[54] INSECTICIDAL, ACARICIDAL, AND NEMATICIDAL O-ETHYL S-ALKYL S-(1,2,4-OXADIAZOL-5-YL-METHYL) PHOSPHORODITHIOLATE DERIVATIVES, COMPOSITIONS, AND METHODS OF USE

[75] Inventors: Akio Kudamatsu, Kawasaki; Toyohiko Kume; Shinichi Tsuboi, both of Hino, all of Japan

[73] Assignee: Nihon Tokushu Noyaku Seizo K.K., Tokyo, Japan

[21] Appl. No.: 441,144

[22] Filed: Nov. 12, 1982

[30] Foreign Application Priority Data

Dec. 7, 1981 [JP] Japan ................. 56-195603

[51] Int. Cl.³ ............... C07F 9/165; C07D 271/06; A61K 33/42
[52] U.S. Cl. ............... 514/92; 71/3; 252/301.28; 548/119; 548/131
[58] Field of Search ........ 548/131, 119; 424/200; 71/3; 252/301.28

[56] References Cited

U.S. PATENT DOCUMENTS

| 3,432,519 | 3/1969 | Metivier et al. | 260/307 |
| 3,910,942 | 10/1975 | Narayanan et al. | 548/131 |
| 4,028,377 | 6/1977 | Meyer et al. | 548/131 |
| 4,237,121 | 12/1980 | King et al. | 424/200 |

FOREIGN PATENT DOCUMENTS

| 1093547 | 5/1966 | United Kingdom | 548/131 |
| 1213707 | 11/1970 | United Kingdom | 424/200 |

Primary Examiner—Henry R. Jiles
Assistant Examiner—J. G. Mullins
Attorney, Agent, or Firm—Sprung, Horn, Kramer & Woods

[57] ABSTRACT

An organophosphate of the formula

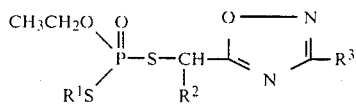

wherein
R¹ is an alkyl group containing 3 to 4 carbon atoms or an alkoxyethyl group having an alkoxy moiety containing 1 to 4 carbon atoms,
R² is a hydrogen atom or a methyl group, and
R³ is an alkyl group containing 1 to 4 carbon atoms or a phenyl group which may be substituted by at least one member selected from the group consisting of a halogen atom, a trifluoromethyl group, a nitro group, an alkyl group containing 1 to 4 carbon atoms, and an alkoxy group containing 1 to 4 carbon atoms, which possesses pesticidal, e.g. insecticidal, acaricidal and nematocidal, activity.

14 Claims, No Drawings

INSECTICIDAL, ACARICIDAL, AND NEMATICIDAL O-ETHYL S-ALKYL S-(1,2,4-OXADIAZOL-5-YL-METHYL) PHOSPHORODITHIOLATE DERIVATIVES, COMPOSITIONS, AND METHODS OF USE

DETAILED DESCRIPTION OF THE INVENTION

This invention relates to novel organophosphates, process for their preparation, and insecticides, acaricides and nematocides containing same.

More particularly, the present invention relates to novel organophosphates represented by the following formula (I):

$$\begin{array}{c} CH_3CH_2O \\ \diagdown \\ R^1S \end{array} \!\!\! \underset{\displaystyle \|}{\overset{\displaystyle O}{P}} \!\!- S - \underset{R^2}{\overset{|}{CH}} \!\!\! \underset{N}{\overset{O-\!\!\!-\!\!\!-N}{\diagup\!\!\!\diagdown}} \!\!\! R^3 \quad (I)$$

wherein

R$^1$ represents an alkyl group containing 3 to 4 carbon atoms, or an alkoxyethyl group having an alkoxy moiety containing 1 to 4 carbon atoms, R$^2$ represents a hydrogen atom or a methyl group, and R$^3$ represents an alkyl group containing 1 to 4 carbon atoms, or a phenyl group which may be substituted by at least one member selected from the group consisting of a halogen atom, a trifluoromethyl group, a nitro group, an alkyl group containing 1 to 4 carbon atoms, and an alkoxy group containing 1 to 4 carbon atoms.

The compounds of the present invention can be prepared by the following process, which the present invention also relates to. That is, it is a process for preparing organophosphates represented by the foregoing general formula (I), which comprises reacting a dithiophosphate or a salt thereof represented by the following general formula:

$$\begin{array}{c} CH_3CH_2O \\ \diagdown \\ R^1S \end{array} \!\!\! \underset{\displaystyle \|}{\overset{\displaystyle O}{P}} \!\!- S - M \quad (II)$$

(wherein R$^1$ is the same as defined above, and M represents a hydrogen atom, an alkali metal atom or an ammonium group)
with a compound represented by the following general formula:

$$Hal - \underset{R^2}{\overset{|}{CH}} \!\!\! \underset{N}{\overset{O-\!\!\!-\!\!\!-N}{\diagup\!\!\!\diagdown}} \!\!\! R^3 \quad (III)$$

(wherein R$^2$ and R$^3$ are the same as defined above, and Hal represents a halogen atom).

Further, the present invention relates to insecticides, acaricides or nematocides containing as effective ingredients the organophosphates of the foregoing general formula (I).

U.S. Pat. No. 4,237,121 gives descriptions relating to the method of using compounds represented by the following general formula:

$$R^1 \!\!\! \underset{N}{\overset{O-\!\!\!-\!\!\!-N}{\diagup\!\!\!\diagdown}} \!\!\! \underset{CH_2X}{\overset{Y}{-}} \!\!\! \underset{\underset{VR^3}{|}}{\overset{\displaystyle \|}{P}} \!\!- ZR^2 \quad (IV)$$

(wherein R$^1$, R$^2$, and R$^3$ each represents an alkyl group containing 1 to 4 carbon atoms, and X, Y, V and Z each represents an oxygen or sulfur atom)
to control particular harmful insects of Diabrotica genus.

U.S. Pat. No. 3,432,519 (corresponding to Japanese Patent Publication No. 24,600/69) describes that compounds represented by the following general formula:

$$R \!\!\! \underset{N\diagdown_O}{\overset{-\!\!\!-\!\!\!-N}{\diagup\!\!\!\diagdown}} \!\!\! CH_2 - S - \overset{\overset{\displaystyle X}{\|}}{P}(OR_1)_2 \quad (V)$$

(wherein R represents an alkyl group containing 1 to 6 carbon atoms which may have an alkoxy group containing 1 to 4 carbon atoms, or a phenyl group which may have one, two or more substituents selected from among a chlorine atom, a nitro group and an alkoxy group containing 1 to 4 carbon atoms, R$^1$ represents an alkyl group containing 1 to 4 carbon atoms, and X represents an oxygen or sulfur atom)
possess insecticidal and acaricidal activities.

The inventors have long made investigations on typical insecticides of organophosphates and, as a result, have now successfully synthesized novel organophosphates represented by the foregoing general formula (I) and not described in known literatures, and have found that the compounds (I) show unexpectedly excellent specific bioactivity.

Investigations by the inventors have revealed that the organophosphates of the foregoing general formula (I) show extremely excellent controlling effects on harmful insects, ticks, and nematodes in agriculture and horticulture, and that the harmful insects-controlling effect of the compounds (I) is much better than those of compounds of analogous chemical structure described in the aforesaid patents.

The compounds of the present invention have the following structural aspects: (i) they have the fundamental skeleton of dithiophosphoric acid $$\begin{array}{c} HO \\ \diagdown \\ HS \end{array} \!\!\! \underset{\displaystyle \|}{\overset{\displaystyle O}{P}} \!\!- SH$$

forming the O-ethyl ester, (ii) the dithiophosphoric acid skeleton further forms an S-alkyl (containing 3 to 4 carbon atoms) ester or S-alkoxy (containing 1 to 6 carbon atoms)- ethyl ester, preferably S-n-propyl ester, S-sec-butyl ester or S-ethoxyethyl ester, and (iii) the remaining sulfur atom of the dithiophosphoric acid skeleton is used to form the S-3-substituted-1,2,4-oxadiazol-5-yl methyl ester or S-1-(3-substituted-1,2,4-oxadiazol-5-yl) ethyl-ester.

The compounds of the present invention show suitable controlling effects on harmful insects, ticks, and nematodes without causing any phytotoxicity to cultivated plants. Also, the compounds can be used to control a wide variety of harmful insects, plant juice-sucking harmful insects, plant-biting insects, and other vegetable-parasitic harmful insects, insects harmful for storing crops, etc., unsanitary insects, etc. thereby to control and kill them.

Specific examples of controllable insects include:

insects of Coleoptera, such as *Callosobruchus chinensis, Sitophilus zeamais, Tribolium castaneum, Epilachna vigintioctomaculata, Agriotes fuscicollis, Anomala rufocuprea, Leptinotarsa decemlineata, Monochamus alternatus,* and *Lyctus brunneus,* insects of Lepidoptera, such as *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Galleria mellonella,* and *Phyllocnistis citrella,* insects of Hemiptera, such as *Nephotettix cincticeps, Nilaparvata lugens, Pseudococcus comstocki, Unaspis yanonensis, Myzus persicae, Aphis pomi, Rhopalosiphum pseudobrassicae, Stephanitis nashi, Nazara spp., Cimex lectularius, Trialeurodes vaporariorum,* and *Psylla, spp.,* insects of Orthoptera, such as *Blatella germanica, Periplaneta americana, Gryllotalpa africana,* and *Locusta migratoria migratoriodes,* insects of Isoptera, such as *Deucotermes speratus,* and *Coptotermes formosanus,* and insects of Diptera, such as *Musca domestica, Aedes aegypti Culex pipiens, Anopheles slnensis, Culex tritaeniorhynchus,* etc.

Specific examples of ticks include: *Tetranychus cinnabarinus, Panonychus citri, Aculus pelekassi,* and *Torronomus spp.*

Specific examples of nematodes include: *Meloidogyne incognita, Aphelenchoides besseyi, Bursaphelenchus lignicolus, Heterodera glycines,* and *Pratylenchus spp.*

In the field of veterinary medicine, the compounds of the present invention are effective for various harmful animal parasites (internal and external parasites), such as ticks, insects and helminthes.

Specific examples of the ticks include: *Oranithodoros spp., Ixodes spp.,* and *Boophilus spp.*

Specific examples of the insects include: *Gastrophilus spp., Stomoxys spp., Trichodectes spp.,* and *Ctenocephalides canis.*

The compounds of the present invention can be prepared, for example, by the following process:

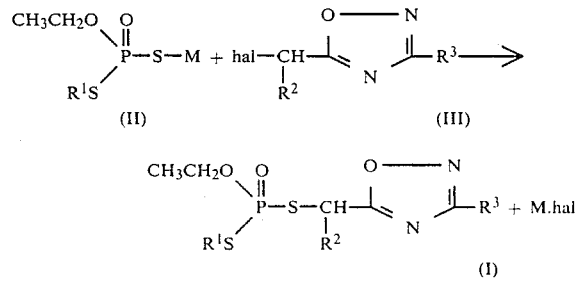

wherein $R^1$, $R^2$, $R^3$, M and hal are the same as defined hereinbefore.

In the above reaction scheme, examples of $R^1$ include an alkyl group containing 3 to 4 carbon atoms such as a n-propyl group, an isopropyl group or a n- (iso-, sec- or tert-) butyl group, and an alkoxyethyl group having an alkoxy moiety containing 1 to 4 carbon atoms such as methoxy, ethoxy, propoxy, isopropoxy or n- (iso-, sec- or tert-) butoxy, examples of $R^2$ include a hydrogen atom and a methyl group, and examples of $R^3$ include an alkyl group containing 1 to 4 carbon atoms such as a methyl group, an ethyl group, a n-propyl group, an iso-propyl group or a n- (iso-, sec- or tert-) butyl group and an optionally substituted phenyl group. As the substituent which said phenyl group optionally has, there may be at least one member selected from the group consisting of a halogen atom such as a fluorine atom, a chlorine atom, a bromine atom or an iodine atom, a trifluoromethyl group, a nitro group, an alkyl group containing 1 to 4 carbon atoms as set forth hereinbefore, and an alkoxy group containing 1 to 4 carbon atoms as set forth hereinbefore.

Specific examples of the dithiophosohoric acid or the salt thereof of general formula (II) to be used as a starting material for the above-described reaction scheme to prepare the compound of the present invention include:
O-ethyl S-propyl hydrogen phosphorodithiolate;
O-ethyl S-sec-butyl hydrogen phosphorodithiolate; and
O-ethyl S-ethoxyethyl hydrogen phosphorodithiolate.

Also, alkali metal salts thereof such as sodium salts and potassium salts, and ammonium salts can be used.

Specific examples of the compounds of general formula (III) to be similarly used as the starting material include:
3-methyl-1,2,4-oxadiazol-5-ylmethyl chloride;
1-(3-methyl-1,2,4-oxadiazol-5-yl)ethyl chloride;
3-phenyl-1,2,4-oxadiazol-5-ylmethyl chloride;
1-(3-phenyl-1,2,4-oxadiazol-5-yl)ethyl chloride;
3-(4-chlorophenyl)-1,2,4-oxadiazol-5-ylmethyl chloride;
1-[3-chlorophenyl)-1,2,4-oxadiazol-5-yl]ethyl chloride;
3-(3-trifluoromethylphenyl)-1,2,4-oxadiazol-5-ylmethyl chloride;
3-(4-nitrophenyl)-1,2,4-oxadiazol-5-ylmethyl chloride;
3-p-tolyl-1,2,4-oxadiazol-5-ylmethyl chloride;
3-(4-methoxyphenyl)-1,2,4-oxadiazol-5-ylmethyl chloride;
3-(4-bromophenyl)-1,2,4-oxadiazol-5-ylmethyl chloride;
3-(4-propylphenyl)-1,2,4-oxadiazol-5-ylmethyl chloride;
1-(3-isopropyl-1,2,4-oxadiazol-5-yl)ethyl chloride;
3-isopropyl-1,2,4-oxadiazol-5-ylmethyl chloride;
1-(3-ethyl-1,2,4-oxadiazol-5-yl)ethyl chloride;
1-(3-propyl-1,2,4-oxadiazol-5-yl)ethyl chloride;
1-(3-sec-butyl-1,2,4-oxadiazol-5-yl)ethyl chloride; and
1-(3-tert-butyl-1,2,4-oxadiazol-5-yl)ethyl chloride.

Furthermore, bromides corresponding to the above-illustrated chlorides can be used in place of the chlorides.

The process for preparing the compounds of the present invention will be specifically described below by reference to a typical example.

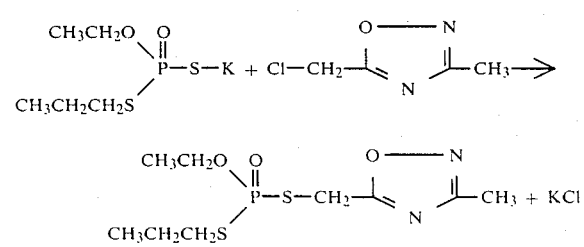

The process for preparing the compounds of the present invention can be conducted desirably using a solvent or diluent. As such solvent or diluent, any inert diluent or solvent can be used.

Such solvent or diluent includes water; aliphatic or aromatic hydrocarbons (optionally chlorinated) such as hexane, cyclohexan, petroleum ether, ligroin, benzene, toluene, xylene, methylene chloride, chloroform, carbon tetrachloride, ethylene chloride, trichloroethylene, chlorobenzene, etc.; ethers such as diethyl ether, methyl ethyl ether, di-iso-propyl ether, dibutyl ether, propylene oxide, dioxane, tetrahydrofuran, etc.; ketones such as acetone, methyl ethyl ketone, methyl isobutyl ketone, etc.; nitriles such as acetonitrile, propionitrile, acrylonitrile, etc.; alcohols such as methanol, ethanol, isopropanol, butanol, ethylene glycol, etc.; esters such as ethyl acetate, amyl acetate, etc.; acid amides such as dimethylformamide, dimethylacetamide, etc.; sulfones and sulfoxides such as dimethylsulfoxide, sulfolane, etc.; and bases such as pyridine, etc.

As is described above, the reaction of the present invention can be carried out in the presence of an acid-binding agent. As such acid-binding agent, there are illustrated generally used hydroxides, carbonates, bicarbonates, and alcoholates of alkali metals, and tertiary amines such as triethylamine, diethylaniline, pyridine, etc.

The process of this invention can be practiced at temperatures of wide range, generally between $-20°$ C. and a boiling point of reaction mixture, desirably between about 0° C. and about 100° C. The reaction is desirably conducted under ordinary pressure, but may be carried out under pressure or under reduced pressure.

In applying the compounds of the present invention as insecticides, acaricides or nematocides, they can be applied by directly diluting with water or in various forms according to methods popularly employed in agricultural fields using agrochemical adjuvants. Upon application, such insecticides, acaricides or nematocides in various application forms may be directly used as such or may be used by diluting with water to a desired concentration.

As the above-described agrochemical adjuvants, there are illustrated, for example, diluents (solvents, diluents, and carriers), surfactants (solubilizing agents, emulsifiers, dispersants, and wetting spreaders), stabilizers, adhesives, propellants for aerosols, synergists, etc.

The solvents include water; and organic solvents such as hydrocarbons (e.g., n-hexan, petroleum ether, naphtha, petroleum factions (paraffin wax, kerosene, gas oil, middle oil, heavy oil, etc.), benzene, toluene, xylene, etc., halogenated hydrocarbons (e.g., methylene chloride, carbon tetrachloride, trichloroethylene, ethylene chloride, ethylene dibromide, chlorobenzene, chloroform, etc.), alcohols (e.g., methyl alcohol, ethyl alcohol, propyl alcohol, ethylene glycol, etc.), ethers (e.g., ethyl ether, ethylene oxide, dioxane, etc.), alcohol ethers (e.g., ethylene glycol monomethyl ether), ketones (e.g., acetone, isophorone, etc.), esters (e.g., ethyl acetate, amyl acetate, etc.), amides (e.g., dimethylformamide, dimethylacetamide, etc.), sulfoxides (e.g., dimethylsulfoxide, etc.), etc.

The diluents or carriers include inorganic fine powders such as slaked lime, magnesium lime, gypsum, calcium carbonate, silica, pearlite, pumice, calcite, diatomaceous earth, amorphous silicon oxide, alumina, zeolite, clay minerals (e.g., pyrophyllite, talc, montmorylonite, beidellite, vermiculite, caolinite, mica); vegetable fine powders such as husk powder, starch, processed starch, sugar, glucose, vegetable stem crush; and synthetic resin fine powders such as phenol resin, urea resin, and vinyl chloride resin.

The surfactants include anionic surfactants such as alkyl sulfates (e.g., sodium lauryl sulfate, etc.), arylsulfonates (e.g., alkylarylsulfonates, sodium alkylnaphthalenesulfonates, etc.), succinic acids, and polyethylene glycol alkylary ether sulfuric esters; cationic surfactants such as alkylamines (e.g., laurylamine, stearyltrimethylammonium chloride, alkyldimethylbenzylammonium chloride, etc.), and polyoxyethylene alkylamines; nonionic surfactants such as polyethylene glycol ethers (e.g., polyoxyethylene alkylaryl ethers and the condensates thereof), polyoxyethylene glycol esters (e.g., polyoxyethylene fatty acid esters, etc.), polyhydric alcohol esters (e.g., polyoxyethylene sorbitan monolaurate), and amphoteric surfactants.

In addition, there can be used stabilizers, adhesive agents (e.g., agricultural soaps, casein limes, sodium alginate, polyvinyl alcohol (PVA), vinyl acetate type adhesive, acrylic adhesive, etc.), propellants for aerosol (e.g., trichlorofluoromethane, dichlorofluromethane, 1,2,2-trichloro-1,1,2-trifluoroethane, chlorobenzene, LNG, lower ether, etc.), combustion-controlling agents (for smoke generators) (e.g., nitrites, zinc dust, dicyandiamide, etc.), oxygen-supplying agents (e.g., chlorates, dichromates, etc.), phytotoxicity-reducing agents (e.g., zinc sulfate, ferrous chloride, copper sulfate, etc.), effect-prolonging agents, dispersion stabilizers (e.g., casein, tragacanth, carboxymethyl cellulose (CMC), polyvinyl alcohol (PVA), etc.), and synergistic agents.

The compounds of the present invention can be made into various application forms in manner generally employed in the field of manufacturing agricultural chemicals. Examples of the application forms or preparations include emulsifiable concentrates, oils, wettable powders, soluble powders, flowables, dusts, granules, smoke generators, tablets, aerosols, pastes, capsules, etc. The insecticides, acaricides and nematocides of the present invention can contain about 0.1 to about 95 wt % of the aforesaid ingredient.

In actual application, the content of active compound in the aforesaid various application forms or preparations and in ready-to-use-preparations generally ranges from about 0.0001 to 20 wt %, preferably from 0.005 to about 10 wt %.

The content of active compound can be properly altered according to the application form, manner, purpose, stage, and place of application, and the state of generation of harmful insects.

The compounds of the present invention can be, if necessary, used in the copresence of, or in combination with, other agrochemicals such as insecticides, fungicides, araricides, nematocides, antiviral agents, herbicides, plant growth regulators, attractants (for example, organophosphates, carbamate type compounds, dithio(or thiol)carbamate type compounds, organic chlorine compounds, dinitro compounds, organosulfur or organometallic compounds, antibiotics, substituted diphenyl ether compounds, urea type compounds, triazole type compounds, etc.) and/or fertilizers.

The various application-formed biocides or ready-to-use-preparations containing the aforesaid active ingredient of the present invention can be applied in manner generally employed in the agricultural field, for example, spraying (e.g., solution spraying), misting, atomizing, dusting, granule distribution, application to water surface, pouring, smoking, application to soil (e.g., mixing, sprinkling, vaporizing, pouring, etc.), surface application (e.g., coating, banding, dusting, covering, dipping, etc.). Further, the so-called ultra-low-volume application method is also employable. In this method, the content of active ingredient can be 100%.

The active compound can be used in an amount of about 0.03 to about 10 kg, preferably about 0.3 to about 6 kg, per ha. In special cases, however, the amount may exceed or fall below the above-described range.

Thus, the present invention provides insecticides, acaricides and nematocides containing the compounds of the aforesaid general formula (I) as active ingredients and diluents (solvents and/or diluents and/or carriers) and/or surfactants and, if necessary, stabilizers, adhesives, and synergists.

Further, the present invention provides a method for controlling harmful insects, ticks, and nematodes by applying the compound of aforesaid general formula (I) alone or in combination with a diluent (solvent and/or diluent and/or carrier) and/or surfactant and, if necessary, a stabilizer, an adhesive, and a synergist to harmful insects, ticks, nematodes or to a place where they live or generate.

The present invention will now be described in more detail by reference to examples which, however, are not to be construed as limiting the invention in any way.

EXAMPLE 1

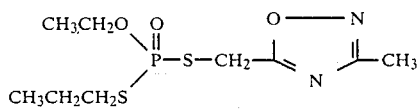

A mixture composed of 7.4 g of potassium O-ethyl S-n-propyl phosphorodithicolate, 3.31 g of 3-methyl-1,2,4-oxadiazol-5-ylmethyl chloride, and 50 ml of acetonitrile was stirred at 40° to 50° C. for 7 hours. After distilling off acetonitrile, 50 ml of water was added to the residue, an oily product produced after stirring was extracted with 60 ml of toluene. The toluene extract was washed twice each with 50 ml of a sodium hydrogencarbonate-saturated aqueous solution. After further washing with water, the organic layers were separated out, and dehydrated with anhydrous sodium sulfate. After distilling off toluene, the residue was distilled under reduced pressure to give 5.2 g of a pale yellow end product of O-ethyl S-n-propyl S-3-methyl-1,2,4-oxadiazol-5-ylmethyl) phosphorodithiolate. b.p. 155°–158° C./0.15 mmHg.

Typical examples of the compounds of this invention synthesized in substantially the same manner as described above are tabulated in Table 1.

TABLE 1

General structure: CH₃CH₂O, R¹S — P(=O) — S — CH(R²) — [1,2,4-oxadiazol] — R³

| Compound No. | R¹ | R² | R³ | Physical Constant |
|---|---|---|---|---|
| 2 | sec-C₄H₉ | H | —CH₃ | $n_D^{20}$ 1.5150 |
| 3 | C₂H₅OC₂H₄— | H | —CH₃ | $n_D^{20}$ 1.5165 |
| 4 | n-C₃H₇ | —CH₃ | —CH₃ | b.p. 150–153° C./ 0.2 mmHg; $n_D^{20}$ 1.5137 |
| 5 | sec-C₄H₉ | —CH₃ | —CH₃ | $n_D^{20}$ 1.5098 |
| 6 | C₂H₅OC₂H₄— | —CH₃ | —CH₃ | $n_D^{20}$ 1.5108 |
| 7 | n-C₃H₇ | H | —C₆H₅ | $n_D^{20}$ 1.5682 |
| 8 | sec-C₄H₉ | H | —C₆H₅ | $n_D^{20}$ 1.5590 |
| 9 | C₂H₅OC₂H₄— | H | —C₆H₅ | $n_D^{20}$ 1.5605 |
| 10 | n-C₃H₇ | H | —C₆H₅ | $n_D^{20}$ 1.5600 |
| 11 | n-C₃H₇ | H | —C₆H₄—Cl | $n_D^{20}$ 1.5750 |
| 12 | n-C₃H₇ | —CH₃ | —C₆H₄—Cl | $n_D^{20}$ 1.5630 |
| 13 | n-C₃H₇ | H | —C₆H₄—CF₃ | $n_D^{20}$ 1.5290 |
| 14 | n-C₃H₇ | H | —C₆H₄—NO₂ | $n_D^{20}$ 1.5828 |
| 15 | n-C₃H₇ | H | —C₆H₄—CH₃ | $n_D^{20}$ 1.5650 |
| 16 | n-C₃H₇ | H | —C₆H₄—OCH₃ | $n_D^{20}$ 1.5725 |
| 17 | n-C₃H₇ | —CH₃ | —C₂H₅ | $n_D^{20}$ 1.5100 |
| 18 | n-C₃H₇ | —CH₃ | n-C₃H₇ | $n_D^{20}$ 1.5068 |
| 19 | n-C₃H₇ | —CH₃ | iso-C₃H₇ | $n_D^{20}$ 1.5064 |
| 20 | n-C₃H₇ | H | iso-C₃H₇ | $n_D^{20}$ 1.5117 |
| 21 | sec-C₄H₉ | —CH₃ | iso-C₃H₇ | $n_D^{20}$ 1.5052 |
| 22 | n-C₃H₇ | —CH₃ | sec-C₄H₉ | bp. 170–173° C./ 1.0 mmHg |
| 23 | n-C₃H₇ | —CH₃ | tert-C₄H₉ | $n_D^{20}$ 1.5004 |

The following examples show how to formulate the novel compounds, the compound numbers having reference to Example 1 and Table 1:

EXAMPLE 2

(Wettable powder)

15 parts of compound No. 1 of the present invention, 80 parts of a mixture of white carbon (hydrous, amorphous silicon oxide fine dust) and powdery clay (1:5), 2 parts of sodium alkylbenzenesulfonate, and 3 parts of sodium alkylnapthalenesulfonate-formalin condensate were pulverized and mixed to prepare a wettable powder. This was diluted with water and sprayed over harmful insects, ticks and nematodes or to a place where they lived or reproduced.

EXAMPLE 3

(Emulsifiable concentrate)

30 parts of compound No. 4 of the present invention, 55 parts of xylene, 8 parts of polyoxyethylene alkylphenyl ether, and 7 parts of calcium alkylbenzesulfonate were mixed and stirred to prepare an emulsifiable concentrate. This was diluted with water and distributed over harmful insects, ticks and nematodes, and/or their habitat or where they reproduced.

EXAMPLE 4

(Dust)

2 Parts of compound No. 6 of the present invention and 98 parts of powdery clay were pulverized and mixed to prepare a dust. This was distributed over harmful insects, ticks, nematodes and/or their habitat or where they reproduced.

EXAMPLE 5

(Dust)

1.5 Parts of compound 7 of the present invention, 0.5 part of isopropyl hydrogen phosphate (PAP), and 98 parts of powdery clay were pulverized and mixed to prepare a dust. This was distributed over harmful insects, ticks, nematodes and/or their habitat or where they reproduced.

EXAMPLE 6

(Granules)

To a mixture of 10 parts of compound No. 10 of the present invention, 30 parts of bentonite (montmorillonite), 58 parts of talc, and 2 parts of ligninsulfonate was added 25 parts of water and, after well kneading, granulated into 10- to 40-mesh granules using an extrusion type granulator and dried at 40 to 50° C. to prepare granules. They were distributed over harmful insects, ticks, nematodes and/or their habitat or to where they reproduced.

EXAMPLE 7

(Granules)

95 Parts of clay mineral particles having a particle size distribution of 0.2 to 2 mm was placed in a rotary mixer and, under rotation, 5 parts of oily compound No. 12 of the present invention was sprayed thereover to be uniformly absorbed, granules thus being prepared. They were distributed over harmful insects, ticks, nematodes and/or their habitat or to a place where they reproduced.

EXAMPLE 8

(Oil)

0.5 Part of compound No. 13 of the present invention and 99.5 parts of kerosene were mixed and stirred to prepare an oil. This was applied to harmful insects, ticks, nematodes and/or their habitat or to a place where they reproduced.

In comparison with known active compounds having analogous structure and with similarly active compounds, the novel compounds of the present invention show substantially improved effects with extremely low toxicity to warm-blooded animals, thus being quite valuable.

Unexpectedly excellent aspects and remarkable effects of the active compounds of the present invention can be seen from the following results obtained by applying them to various harmful insects, ticks, and nematodes.

The novel compounds are those of Example 1 and Table 1 while comparative compounds have the following structures:

Comparative compound IV-1:

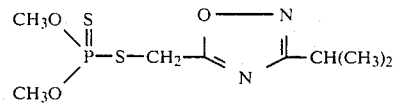

(described in U.S. Pat. No. 4,237,121)

Comparative compound V-1:

$$\begin{array}{c} CH_3CH_2O \\ \diagdown \\ CH_3CH_2O \end{array} \!\!\! \begin{array}{c} O \\ \| \\ P-S-CH_2 \end{array} \!\!\! \begin{array}{c} N \\ \diagup \\ O \end{array} \!\!\! \begin{array}{c} \diagup \\ \diagdown N \end{array}$$

(described in U.S. Pat. No. 3,432,519 = Japanese Patent Publication No. 24600/69)

EXAMPLE 9

Test for *Spodoptera litura* larvae

Preparation of sample solution:

| Solvent: | Xylene | 3 parts by weight |
|---|---|---|
| Emulsifier: | Polyoxyethylene alkylphenyl ether | 1 part by weight |

In order to obtain preparations of suitable active compounds, 1 part by weight of each active compound was mixed with the above-described amount of the solvent containing the above-described amount of the emulsifier, and the resulting mixture was diluted with water to a predetermined concentration. Sweet potato leaves were dipped in the water-diluted solution containing a predetermined concentration of the active compound and, after air-drying, placed in a petri dish of 9 cm in diameter. Ten 3-instar larvae of *Spodoptera litura* were placed therein, and the dish was placed in a 28° C. thermostatic room. After 24 hours, the number of dead larvae was counted to calculate knock down ratio.

The results thus obtained are shown in Table 2.

TABLE 2

| Compound No. | Effective Ingredient Concentration (ppm) | Knock Down Ratio (%) |
|---|---|---|
| 1 | 300 | 100 |
| 4 | 300 | 100 |
| 6 | 300 | 100 |
| 7 | 300 | 100 |
| 10 | 300 | 100 |
| 12 | 300 | 100 |
| 15 | 300 | 100 |
| 17 | 300 | 100 |
| 18 | 300 | 100 |

TABLE 2-continued

| | Effective Ingredient Concentration (ppm) | Knock Down Ratio (%) |
|---|---|---|
| 19 | 300 | 100 |
| 20 | 300 | 100 |
| 21 | 300 | 100 |
| 22 | 300 | 100 |
| 23 | 300 | 100 |
| Comparative Compound | | |
| IV-1 | 1000 | 80 |
| | 300 | 0 |
| V-1 | 1000 | 0 |

EXAMPLE 10

Test for *Callosobruchus chinensis*

Testing method:

A filter paper was placed in a 9-cm diameter pertri dish, and 1 ml of each water-diluted solution containing a predetermined concentration of the active compound prepared in Example 9 was added thereto. 20 *Callosobruchus chinensis* were placed therein, and the dish was placed in a 28° C. thermostatic room. After 24 hours, the number of dead insects was counted to calculate knock down ratio.

The results thus obtained are shown in Table 3.

TABLE 3

| | Effective Ingredient Concentration (ppm) | Knock Down Ratio (%) |
|---|---|---|
| Compound No. | | |
| 5 | 10 | 100 |
| 8 | 10 | 100 |
| 10 | 10 | 100 |
| 11 | 10 | 100 |
| 12 | 10 | 100 |
| 13 | 10 | 100 |
| 16 | 10 | 100 |
| 19 | 10 | 100 |
| Comparative Compound | | |
| IV-1 | 10 | 0 |
| V-1 | 10 | 0 |

EXAMPLE 11

Test for organophosphorus insecticide-resistant *Nephotettix cincticeps*

Testing method:

Each water-diluted solution containing a predetermined amount of the active compound prepared as in Example 9 was sprayed over rice of about 10 cm in height planted in a 12-cm diameter pot. After drying the sprayed solution, the pot was covered by a wire cage 7 cm in diameter and 14 cm in height, containing 30 female adult *Nephotettix cincticeps* resistant against organophosphorus insecticides. After being placed in a thermostatic room for 24 hours, the number of dead insects was counted to calculate knock down ratio.

The results thus obtained are shown in Table 4.

TABLE 4

| | Effective Ingredient Concentration (ppm) | Knock Down Ratio (%) |
|---|---|---|
| Compound No. | | |
| 1 | 100 | 100 |
| 2 | 100 | 100 |
| 4 | 100 | 100 |
| 5 | 100 | 100 |
| 6 | 100 | 100 |
| 8 | 100 | 100 |
| 10 | 100 | 100 |
| 11 | 100 | 100 |
| 12 | 100 | 100 |
| 13 | 100 | 100 |
| 14 | 100 | 100 |
| 16 | 100 | 100 |
| 17 | 100 | 100 |
| 18 | 100 | 100 |
| 20 | 100 | 100 |
| 21 | 100 | 100 |
| 22 | 100 | 100 |
| 23 | 100 | 100 |
| Comparative Compound | | |
| IV-1 | 1000 | 0 |
| V-1 | 1000 | 0 |

EXAMPLE 12

Test for *Musca domestica*

Testing method:

A filter paper was placed in a 9-cm diameter petri dish, and 1 ml of each water-diluted sample solution containing a predetermined concentration of the active compound prepared as in Example 9 was added thereto. Ten female adult *Musca domestica* resistant against organophosphorus insecticides were placed therein, and the dish was placed in a 28° C. thermostatic room. After 24 hours, the number of dead insects was counted to calculate knock down ratio.

The results thus obtained are shown in Table 5.

TABLE 5

| | Effective Ingredient Concentration (ppm) | Knock Down Ratio (%) |
|---|---|---|
| Compound No. | | |
| 1 | 1000 | 100 |
| 2 | 1000 | 100 |
| 4 | 1000 | 100 |
| 5 | 1000 | 100 |
| 7 | 1000 | 100 |
| 8 | 1000 | 100 |
| 13 | 1000 | 100 |
| 14 | 1000 | 100 |
| 15 | 1000 | 100 |
| 16 | 1000 | 100 |
| 17 | 1000 | 100 |
| 18 | 1000 | 100 |
| 19 | 1000 | 100 |
| 20 | 1000 | 100 |
| 21 | 1000 | 100 |
| 23 | 1000 | 100 |
| Comparative Compound | | |
| IV-1 | 1000 | 40 |

EXAMPLE 13

Test for *Tetranychus cinnabarinus* (by distribution)

Testing method:

50 to 100 adult *Tetranychus cinnabarinus* resistant against organophosphorus acaricides were applied to the leaves of two-leaf stage kidney beans. After two days waiting, a water-diluted sample solution containing a predetermined concentration of the active compound prepared as in Example 9 was distributed over the leaves in an amount of 40 ml per pot. After being left for ten days in a greenhouse, controlling effects were evaluated in terms of the following indexes:

3: Living adult insects: 0%
2: Living adult insects: more than 0% and less than 5% of those in untreated area
1: Living adult insects: 5 to 50% of those in untreated area
0: Living adult insects: more than 50% of those in untreated area The results thus obtained are shown in Table 6.

TABLE 6

| Compound No. | Effective Ingredient Concentration (ppm) | Controlling Index |
|---|---|---|
| 1 | 100 | 3 |
| 4 | 100 | 3 |
| 5 | 100 | 3 |
| 6 | 100 | 3 |
| 7 | 100 | 3 |
| 8 | 100 | 3 |
| 9 | 100 | 3 |
| 10 | 100 | 3 |
| 11 | 100 | 3 |
| 12 | 100 | 3 |
| 13 | 100 | 3 |
| 15 | 100 | 3 |
| 16 | 100 | 3 |
| 17 | 100 | 3 |
| 18 | 100 | 3 |
| 19 | 100 | 3 |
| 20 | 100 | 3 |
| 21 | 100 | 3 |
| 22 | 100 | 3 |
| 23 | 100 | 3 |
| Comparative Compound | | |
| IV-1 | 1000 | 0 |
| V-1 | 1000 | 0 |

Testing method:

A filter paper was placed in a 9-cm diameter pertri dish, and 1 ml of a water-diluted sample solution containing a predetermined concentration of the active compound prepared as in Example 9 was added thereto. 10 adult *Blatella germanica* were placed therein and left in a 28° C. thermostatic room. After 24 hours, the number of dead insects was counted to calculate knock down ratio.

The results thus obtained are shown in Table 7.

TABLE 7

| Compound No. | Effective Ingredient Concentration (ppm) | Knock Down Rate (%) |
|---|---|---|
| 1 | 1000 | 100 |
| 2 | 1000 | 100 |
| 3 | 1000 | 100 |
| 4 | 1000 | 100 |
| 5 | 1000 | 100 |
| 6 | 1000 | 100 |
| 7 | 1000 | 100 |
| 8 | 1000 | 100 |
| 10 | 1000 | 100 |
| 12 | 1000 | 100 |
| 13 | 1000 | 100 |
| 14 | 1000 | 100 |
| 15 | 1000 | 100 |
| 16 | 1000 | 100 |

TABLE 7-continued

| | Effective Ingredient Concentration (ppm) | Knock Down Rate (%) |
|---|---|---|
| 17 | 1000 | 100 |
| 18 | 1000 | 100 |
| 19 | 1000 | 100 |
| 20 | 1000 | 100 |
| 21 | 1000 | 100 |
| 22 | 1000 | 100 |
| 23 | 1000 | 100 |
| Comparative Compound | | |
| IV-1 | 1000 | 0 |
| V-1 | 1000 | 0 |

EXAMPLE 15

Test for *Culex pipens* larvae

Testing method:

100 ml of a water-diluted solution containing a predetermined concentration of the active compound prepared as in Example 9 was placed in a 9-cm deep petri dish, and 25 4-instar *Culex pipiens* larvae were released therein and left in a 28° C. thermostatic room. After 24 hours, the number of dead insects was counted to calculate knock down ratio.

The results thus obtained are shown in Table 8.

TABLE 8

| Compound No. | Effective Ingredient Concentration (ppm) | Knock Down Ratio (%) |
|---|---|---|
| 2 | 0.1 | 100 |
| 7 | 0.1 | 100 |
| 8 | 0.01 | 100 |
| 10 | 0.1 | 100 |
| 11 | 0.01 | 100 |
| 12 | 0.01 | 100 |
| 13 | 0.01 | 100 |
| 14 | 0.01 | 100 |
| 15 | 0.01 | 100 |
| 16 | 0.1 | 100 |
| 21 | 0.1 | 100 |
| Comparative Compound | | |
| IV-1 | 0.1 | 0 |
| V-1 | 0.1 | 0 |

EXAMPLE 16

Test for *Meloidogyne incognita*

Preparation of sample solution:

2 parts of an active compound and 98 parts of talc were pulverized and mixed with each other.

Testing method:

The above-described sample was applied to soil infested with *Meloidogyne incognita* in an amount of 50, 25, 10 or 5 ppm, and uniformly stirred to mix, followed by filling the thus treated soil in a 1/5000-a pot. Then, the soil was seeded with about 20 tomato seeds (kind: Kurihara), followed by cultivating in a greenhouse. After 4 weeks, the tomato samples were drawn without damaging roots, and the degree of damage of 10 tomato samples was rated according to the following standard to determine root gall index:

Degree of damage
0: no galls (completely controlled)
1: slight galls
3: many galls 4: the most galls (corresponding to untreated case)

$$\text{Root gall index} = \frac{\Sigma(\text{Class mark} \times \text{Individual number})}{\text{Total rated individual number} \times 4} \times 100$$

Additionally, the rating was presented in terms of the controlling effect determined according to the following formula:

$$\text{Controlling effect} = \frac{(\text{Root gall index in untreated area} - \text{Root gall index in treated area})}{\text{Root gall index in untreated area}} \times 100$$

Controlling effect of 100% means complete control. The results thus obtained are shown in Table 9.

TABLE 9

| | Effective Ingredient Concentration (ppm) | Controlling Effect (%) |
|---|---|---|
| Compound No. | | |
| 1 | 50 | 100 |
| 7 | 50 | 100 |
| Comparative Compound | | |
| IV-1 | 50 | 0 |
| V-1 | 50 | 0 |

It will be appreciated that the instant specification and examples are set forth by way of illustration and not limitation, and that various modifications and changes may be made without departing from the spirit and scope of the present invention.

We claim:

1. An organophosphate of the formula

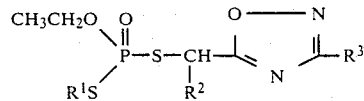

wherein
R¹ is an alkyl group containing 3 to 4 carbon atoms or an alkoxyethyl group having an alkoxy moiety containing 1 to 4 carbon atoms,
R² is a hydrogen atom or methyl group, and
R³ is an alkyl group containing 1 to 4 carbon atoms or a phenyl group which may be substituted by at least one member selected from the group consisting of a halogen atom, a trifluoromethyl group, a nitro group, an alkyl group containing 1 to 4 carbon atoms, and an alkoxy group containing 1 to 4 carbon atoms.

2. An organophosphate according to claim 1, wherein R¹ is a n-propyl group, a sec-butyl group or an ethoxyethyl group.

3. An organophosphate according to claim 1, wherein such compound is 0-ethyl S-n-propyl S-(3-methyl-1,2,4-oxadiazol-5-yl-methyl) phosphorodithiolate of the formula

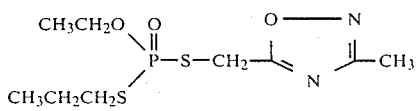

4. An organophosphate according to claim 1, wherein such compound is O-ethyl S-n-propyl S-1-(3-methyl-1,2,4-oxadiazol-5-yl)ethyl phosphorodithiolate of the formula

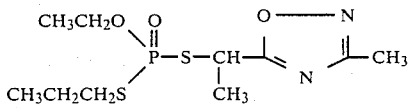

5. An organophosphate according to claim 1, wherein such compound is O-ethyl S-n-propyl S-(3-phenyl-1,2,4-oxadiazol-5-yl-methyl) phosphorodithiolate of the formula

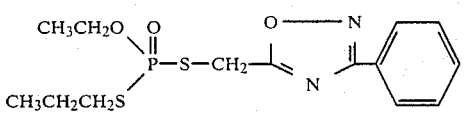

6. An organophosphate according to claim 1, wherein such compound is O-ethyl S-n-propyl S-3-(4-chlorophenyl)-1,2,4-oxadiazol-5-yl-methyl phosphorodithiolate of the formula

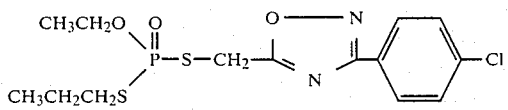

7. An organophosphate according to claim 1, wherein such compound is O-ethyl S-n-propyl S-1-(3-phenyl-1,2,4-oxadiazol-5-yl)-ethyl phosphorodithiolate of the formula

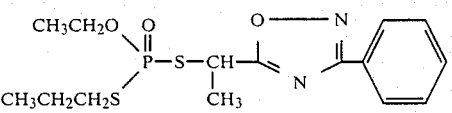

8. An organophosphate according to claim 1, wherein such compound is O-ethyl S-n-propyl S-1-(3-(4-chlorophenyl)-1,2,4-oxadiazol-5-yl)-ethyl phosphorodithiolate of the formula

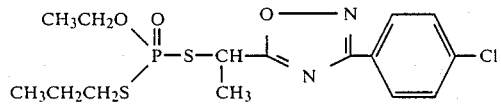

9. An organophosphate according to claim 1, wherein such compound is O-ethyl S-n-propyl S-(3-(3-trifluoromethylphenyl)-1,2,4-oxadiazol-5-yl-methyl) phosphorodithiolate of the formula

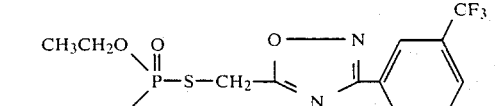

10. An organophosphate according to claim 1, wherein such compound is O-ethyl S-n-propyl S-(3-(4-nitrophenyl)-1,2,4-oxadiazol-5-yl-methyl) phosphorodithiolate of the formula

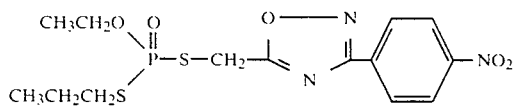

11. An insecticidal, acaricidal or nematocidal composition comprising an insecticidally, acaricidally or nematocidally effective amount of an organophosphate according to claim 1 in admixture with a diluent.

12. A method of combatting insects, acarids or nematodes which comprises applying to such insects, acarids or nematodes, or to a habitat thereof, an insecticidally, acaricidally or nematocidally effective amount of an organophosphate according to claim 1.

13. (Once amended) The method according to claim 12, wherein such organophosphate is O-ethyl S-n-propyl S-(3-methyl-1,2,4-oxadiazol-5-yl-methyl) phosphorodithiolate, O-ethyl S-n-propyl S-1-(3-methyl-1,2,4-oxadiazol-5-yl)-ethyl phosphorodithiolate, O-ethyl S-n-propyl S-(3-phenyl-1,2,4-oxadiazol-5-yl methyl) phosphorodithiolate, O-ethyl S-n-propyl S-3-(4-chlorophenyl)-1,2,4-oxadiazol-5-yl-methyl phosphorodithiolate, 0-ethyl S-n-propyl S-1-(3-phenyl-1,2,4-oxadiazol-5-yl)-ethyl phosphorodithiolate, O-ethyl S-n-propyl S-1-(3-(4-chlorophenyl)-1,2,4-oxxadiazol-5-yl)-ethyl phosphorodithiolate, O-ethyl S-n-propyl S-(3-(3-trifluoromethylphenyl)-1,2,4-oxadiazol-5-yl-methyl) phosphorodithiolate, O-ethyl S-n-propyl S-(3-(4-nitrophenyl)-1,2,4-oxadiazol-5-yl-methyl) phosphorodithiolate, or O-ethyl-S-n-propyl S-1-(3-isopropyl-1,2,4-oxadiazol-5-yl)-ethyl phosphorodithiolate.

14. An organophosphate according to claim 1, wherein such compound is O-ethyl-S-n-propyl S-1-(3-isopropyl-1,2,4-oxadiazol-5-yl)-ethyl phosphorodithiolate of the formula

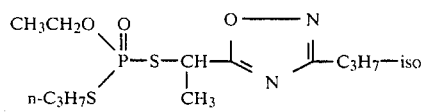

* * * * *

UNITED STATES PATENT AND TRADEMARK OFFICE
CERTIFICATE OF CORRECTION

PATENT NO. : 4,497,804
DATED : February 5, 1985
INVENTOR(S) : Akio Kudamatsu, et al It is certified that error appears in the above-identified patent and that said Letters Patent is hereby corrected as shown below:

| | |
|---|---|
| Col. 2, line 5, Formula (IV) | Delete beginning of formula and substitute: 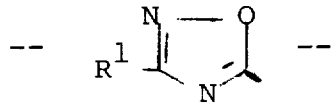 |
| Col. 2, line 60 | Delete "1 to 6" and substitute --1 to 4-- |
| Col. 4, line 16 | Correct spelling of "dithiophosphoric" |
| Col. 4, line 34 | After "1-[3-" insert --(4- -- |
| Col. 5, line 7 | Correct spelling of "cyclohexane" |
| Col. 5, line 50 | Correct spelling of "hexane" |
| Col. 5, line 51 | Correct spelling of "fractions" |
| Col. 6, line 24 | Correct spelling of "dichlorofluoromethane" |
| Col. 6, line 47 | Before "20 wt %" insert --about-- |
| Col. 7, line 38 | Correct spelling of "phosphorodithiolate" |
| Col. 7, line 46 | Delete "layers" and substitute --layer-- |
| Col. 7, line 50 | Delete "S-3-" and substitute -- S-(3- -- |
| Col. 8, Table 1, Compound 10 | Under "R$^2$" delete "H" and substitute -- -CH$_3$-- |

UNITED STATES PATENT AND TRADEMARK OFFICE
CERTIFICATE OF CORRECTION

PATENT NO.  : 4,497,804
DATED       : February 5, 1985
INVENTOR(S) : Akio Kudamatsu, et al It is certified that error appears in the above-identified patent and that said Letters Patent is hereby corrected as shown below:

Col. 8, Table 1, Compound 13    Under "$R^3$" delete formula and substitute:

-- 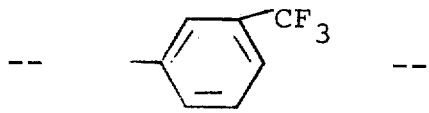 --

Col. 11, line 20    Correct spelling of "petri"
Col. 14, line 18    Correct spelling of "pipiens"
Col. 18, line 6     Correct spelling of "oxadiazol"

Signed and Sealed this

Twentieth Day of August 1985

[SEAL]

Attest:

DONALD J. QUIGG

Attesting Officer    Acting Commissioner of Patents and Trademarks